(12) United States Patent
Pang et al.

(10) Patent No.: US 11,058,609 B2
(45) Date of Patent: Jul. 13, 2021

(54) ADHESIVE PATCH

(71) Applicant: Research & Business Foundation Sungkyunkwan University, Suwon-si (KR)

(72) Inventors: Chang Hyun Pang, Pyeongtaek-si (KR); Da Wan Kim, Suwon-si (KR); Sang Yul Baik, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 16/663,772

(22) Filed: Oct. 25, 2019

(65) Prior Publication Data

US 2020/0163844 A1 May 28, 2020

(30) Foreign Application Priority Data

Nov. 26, 2018 (KR) ........................ 10-2018-0147064

(51) Int. Cl.
| | |
|---|---|
| *A61K 8/00* | (2006.01) |
| *A61K 8/02* | (2006.01) |
| *A61F 13/00* | (2006.01) |
| *A61B 5/00* | (2006.01) |
| *A61K 8/04* | (2006.01) |

(52) U.S. Cl.
CPC .......... *A61K 8/0208* (2013.01); *A61B 5/6833* (2013.01); *A61F 13/00017* (2013.01); *A61F 13/00029* (2013.01); *A61F 13/00034* (2013.01); *A61K 8/042* (2013.01)

(58) Field of Classification Search
CPC ....................................................... A61K 8/42
See application file for complete search history.

(56) References Cited

U.S. PATENT DOCUMENTS 5,486,158 A * 1/1996 Samuelsen .......... A61F 13/0213
602/46

FOREIGN PATENT DOCUMENTS

| KR | 10-2005-0021003 A | 3/2005 |
| KR | 10-2017-0020221 A | 2/2017 |
| KR | 20170020221 A * | 2/2017 |

* cited by examiner

*Primary Examiner* — Benjamin J Packard
(74) *Attorney, Agent, or Firm* — NSIP Law

(57) ABSTRACT

The present invention relates to an adhesive patch. The adhesive patch includes a plurality of reliefs, each relief having a flat top face, and each micro channel groove defined between adjacent reliefs of the plurality of reliefs, wherein the plurality of reliefs and the micro channel groove are respectively formed on and defined the adhesive patch, and wherein a hydrogel layer is disposed on at least a portion of a bottom face of the micro channel groove and is contained in the groove. Therefore, the adhesive patch is well-adhered to a dry or wet adhered face.

21 Claims, 8 Drawing Sheets

ADHESIVE PATCH

CROSS-REFERENCE TO RELATED APPLICATION

This application claims a benefit under 35 U.S.C. § 119(a) of Korean Patent Application No. 10-2018-0147064 filed on Nov. 26, 2018, on the Korean Intellectual Property Office, the entire disclosure of which is incorporated herein by reference for all purposes.

BACKGROUND

1. Field

The present disclosure relates to an adhesive patch and a method for producing the same. Specifically, the present disclosure relates to an adhesive patch that provides a strong adhesive strength in a wet environment, for example, on a sweaty skin surface, without a chemical adhesive.

2. Description of Related Art

Recently, there is a growing interest in patch products that adhere to a skin, such as face masks, skin condition measuring sensor patches, and the like. Accordingly, research on development and improvement of a skin patch is steadily increasing. There is a high demand for improvement of the facial masks chronic problems, such as a problem of not adhering well to a skin due to oil and the like, a problem of not adhering well to a face due to a curved surface of the face, a problem in which ampoule liquid remains and flows, and the like, which are important issues. Further, there is an increasing demand for patches that adhere to the skin in a dry-type adhesion manner without requiring a chemical adhesive. In particular, a demand for the dry-type adhesion in a wet state such as the skin is increasing. Further, as a skin patch, there is a need for improvement of a sensitivity of a bio-signal. Conventional medical tapes have an adhesive strength using a chemical adhesive such as an acrylic compound, which is a chemical. Such chemical adhesive severely peels and damages vulnerable epidermis of a baby or an old person, and the adhesive strength becomes very weak when the medical tape is removed once. In order to solve these problems, researches on a dry-type adhesion system that does not use chemicals for adhesion is actively conducted. The dry-type adhesion system exhibits an adhesive strength by a van der Waals force without using the chemicals. Since a surface damage occurring in adhesion and detachment is low and repeatability is excellent, the dry-type adhesion system is reusable. However, such a dry-type adhesion system also has a problem of poor adhesion in a wet environment.

SUMMARY

The present disclosure may provide an adhesive patch and a method for producing the same that maintain close contact with a skin without damaging an adhered face, particularly the skin, and also have an improved bio-signal sensitivity.

A first aspect of the present disclosure proposes an adhesive patch having a surface portion, wherein the surface portion includes a plurality of reliefs, each relief having a flat top face, and each micro channel groove defined between adjacent reliefs of the plurality of reliefs, wherein the plurality of reliefs and the micro channel groove are respectively formed on and defined in a surface of the adhesive patch, and wherein a hydrogel layer is disposed on at least a portion of a bottom face of the micro channel groove and is contained in the groove.

The present disclosure provides adhesion in a wet environment unpredictable simply by placing a hydrophilic hydrogel between channels on a face of a patterned patch having the micro channels. Even a patterned patch with microchannels provides strong adhesive strength, for example, strong adhesive strength that prevents the patch from easily peeled off from a side, in the wet environment. However, simply by placing the hydrogel, which is hydrophilic than a polymer of the micro channel, in such a micro channel, stronger adhesive strength may be provided in the wet environment compared to a case in which the hydrogel is not placed.

In one implementation, a height of the hydrogel layer from the bottom face of the micro channel groove may be smaller than a height of each relief from the bottom face of the micro channel groove.

In one implementation, a contact angle of a water droplet on the hydrogel layer may be smaller than a contact angle of a water droplet on each relief.

In one implementation, a contact angle of a water droplet on the hydrogel layer may be equal to or smaller than 70°.

In one implementation, the hydrogel layer may absorb and discharge moisture.

In one implementation, the hydrogel layer may include at least one selected from a group consisting of poly acrylamide (PAAm), poly(N-isopropylacrylamide) (PNIPAM), poly ethylene glycol (PEG), chitosan, polyallylamine (PAA), polyethylenimine (PEI), collagen, gelatin, polyampholyte (PA), poly(2-hydroxyethyl methacrylate)-co-poly-(ethylene glycol) diacrylate (PHEMA-co-PEGDA), poly(dimethyl diallyl ammonium chloride)/tannic acid, alginate, and mixtures thereof.

In one implementation, the hydrogel layer may have a hydrophile-lipophile balance (HLB) value of 5 to 20.

In one implementation, each relief may have a hydrophile-lipophile balance (HLB) value of 0 to 15.

In one implementation, each relief may include at least one selected from a group consisting of natural rubber, nitrile rubber, acrylonitrile-butadiene rubber, styrenebutadiene rubber, chloroprene rubber, butyl rubber, isoprene-isobutylene rubber, ethylene propylene rubber, chlorosulphonated polyethylene rubber, acrylic rubber, fluoro rubber, polysulfide rubber, silicone rubber, butadiene rubber, isoprene rubber, urethanerubber, polyurethane, polyolefin thermoplastic elastomer (TPE), polystyrene TPE, polyvinyl chloride TPE, polyester TPE, polyurethane TPE, polyamide TPE, polyethyleneterephthalate (PET), polydimethylsiloxane (PDMS), polyurethaneacrylate, polyethylenenaphthalate (PEN), and mixtures thereof.

In one implementation, the adhesive patch may be adhered to an adhered face, and wherein the adhered face may contain moisture or oil.

In one implementation, the adhesive patch may be adhered to an adhered face, and wherein the adhered face may contain 25 µl or smaller of water per 1 $cm^2$ of the adhered face.

In one implementation, the adhesive patch may be adhered to an adhered face, and wherein a width of each micro channel groove may be sized such that moisture may be sucked into a space between the adhered face and the hydrogel layer in the micro channel groove via a capillary force. Further, the width of each micro channel groove may be in a range of 1 nm to 1000 µm.

In one implementation, the hydrogel layer may be disposed on at least a portion of the bottom face of the micro channel groove and may be contained in the groove such that a vertical adhesive strength of the adhesive patch adhered to the adhered face may be equal to or greater than 1.2 N/cm$^2$.

In one implementation, the hydrogel layer may be disposed on at least a portion of the bottom face of the micro channel groove such that a peel strength energy of the adhesive patch from the adhered face may be equal to or greater than 3 J/m$^2$.

A second aspect of the present disclosure proposes an adhesive patch for delivering a substance, the adhesive patch including the adhesive patch as defined above, wherein the adhesive patch contains a drug, a drug-containing particle, or a cosmetic substance.

In one implementation, the drug, the drug-containing particle, or the cosmetic substance contained in the adhesive patch may be delivered into the skin when the adhesive patch is brought into contact with the skin. Further, the drug, the drug-containing particle, or the cosmetic substance may be contained in a surface of each relief.

A third aspect of the present disclosure proposes an adhesive patch for measuring a bio-signal of a skin, the adhesive patch including the adhesive patch as defined above, wherein the adhesive patch is able to be adhered to a wet adhered face, wherein the adhesive patch further includes a piezoelectric layer adhered to a face of the patch opposite to the surface portion or inserted into the patch such that the piezo electric layer is deformed along with a mechanical deformation of the adhesive patch, and an electrode for receiving an electrical signal from the piezoelectric layer. Each relief includes a conductive polymer to receive the electrical signal.

The present disclosure relates to the adhesive patch. The adhesive patch according to the present disclosure includes the micro channel structure and the hydrogel, so that the moisture may be absorbed and discharged, and irritation on the adhered face may be minimized while maintaining an excellent adhesive strength. Therefore, the adhesive strength is excellent without damaging the skin, the substance is able to be delivered, and a sensitivity of the bio-signal sensor is able to be improved by adding a conductive substance, so that the adhesive patch according to the present disclosure may be applied to adhesive patches and wearable elements of various applications.

DETAILED DESCRIPTIONS

Figure 1:
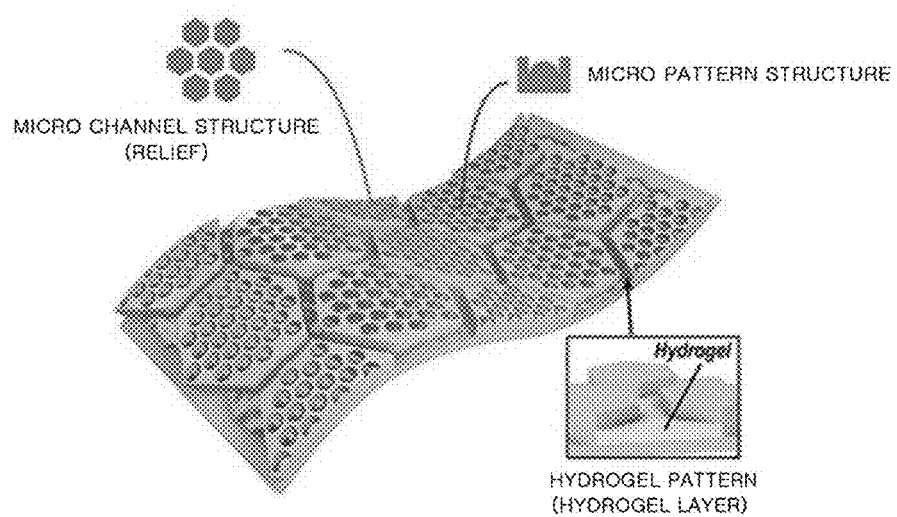
FIG. 1 illustrates a schematic diagram of a patch according to an embodiment of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, components, elements, or combinations thereof, but do not preclude the presence or addition of one or more other features, integers, operations, components, elements, or combinations thereof.

Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A term 'adhesion' used in the present disclosure is attachable and detachable and means that adhesion to an adhered face such that detachment without physical damage on the adhered face is achieved after the adhesion to the adhered face. An adhesive patch according to the present disclosure may be adhered to the adhered face without adhesive or glue.

The adhesive patch according to the present disclosure is an adhesive patch having a surface portion including a plurality of reliefs, each relief having a flat top face, and each micro channel groove defined between adjacent reliefs of the plurality of reliefs. Further, hydrogel is disposed on at least a portion of a bottom face of the micro channel groove and contained in the groove.

In one embodiment, the adhesive patch has a micro channel structure formed thereon. Further, the micro channel structure may include the relief and the micro channel groove.

In one embodiment, on the bottom face of the micro channel groove, the hydrogel may be disposed as a hydrogel layer. In other words, the hydrogel layer containing the hydrogel may be contained in a portion of the micro channel groove, and the hydrogel layer containing the hydrogel may be stacked on the bottom face of the micro channel groove.

In one embodiment, the hydrogel layer may have a pattern. In other words, at least one layer of a pattern containing the hydrogel may be stacked on the bottom face of the micro channel groove.

In one embodiment, the planar shape of each relief may be circular or polygonal, but the present disclosure is not limited thereto. In one embodiment, the planar shapes of the plurality of reliefs may be different from each other or may be the same.

In one embodiment, the hydrogel layer may have a contact angle of a water droplet on the hydrogel layer equal to or smaller than 70°. In other words, the hydrogel layer may be more hydrophilic than the relief.

In one embodiment, the hydrogel layer contains the hydrogel, so that moisture may be absorbed or discharged. In one embodiment, the hydrogel layer may serve as a moisture regulator that may regulate moisture on the adhered face. For example, when the adhesive patch is adhered to a skin surface, the hydrogel layer may absorb sweat, discharge, and the like from the skin. This may further improve an adhesive strength of the adhesive patch. Eventually, the adhesive patch may include a hydrogel inserted portion formed by inserting the hydrogel in the micro channel groove defined by the relief, that is the hydrogel layer, so that the moisture may be absorbed and an adhesive strength for a wet adhered face may be improved.

In one embodiment, the relief may be hydrophobic.

In one embodiment, the hydrogel layer may include at least one selected from a group consisting of poly acrylamide (PAAm), poly(N-isopropylacrylamide) (PNIPAM), poly ethylene glycol (PEG), chitosan, polyallylamine (PAA), polyethylenimine (PEI), collagen, gelatin, polyampholyte (PA), poly(2-hydroxyethyl methacrylate)-co-poly-(ethylene glycol) diacrylate (PHEMA-co-PEGDA), poly(dimethyl diallyl ammonium chloride)/tannic acid, alginate, and mixtures thereof. For example, the hydrogel layer may include one of poly acrylamide, poly(N-isopropylacrylamide), and poly ethylene glycol.

In one embodiment, the relief may include at least one selected from a group consisting of natural rubber, nitrile rubber, acrylonitrile-butadiene rubber, styrenebutadiene rubber, chloroprene rubber, butyl rubber, isoprene-isobutylene rubber, ethylene propylene rubber, chlorosulphonated polyethylene rubber, acrylic rubber, fluoro rubber, polysulfide rubber, silicone rubber, butadiene rubber, isoprene rubber, urethanerubber, polyurethane, polyolefin thermoplastic elastomer (TPE), polystyrene TPE, polyvinyl chloride TPE, polyester TPE, polyurethane TPE, polyamide TPE, polyethyleneterephthalate (PET), polydimethylsiloxane (PDMS), polyurethaneacrylate, polyethylenenaphthalate (PEN), and mixtures thereof. For example, the relief may include one of polyethyleneterephthalate, polydimethylsiloxane, polyurethaneacrylate, polyethylenenaphthalate, and polyurethane.

In one embodiment, the adhered face to which the adhesive patch is adhered may contain the moisture or oil. In one embodiment, the adhered face may contain a water molecule, but the present disclosure is not limited thereto.

In one embodiment, the adhered face may contain 25 ul or smaller of water per 1 cm$^2$ of the adhered face. For example, in one embodiment, the adhered face may contain 22.2 μl or smaller of water per 1 cm$^2$ of the adhered face. For example, the adhered face to which the adhesive patch is adhered may be the skin.

In one embodiment, the flat top face of each relief may include a plurality of micro or nano sized needles or protrusions formed thereon.

In one embodiment, a height of the hydrogel layer from the bottom face of the micro channel groove may be smaller than a height of each relief from the bottom face of the micro channel groove. Further, a width of each micro channel groove may be sized such that moisture is sucked into a space between the face to which the adhesive patch is adhered and the micro channel via a capillary force. For example, the width of the micro channel groove may be in a range of 1 nm to 1000 μm. The adhesive strength of the adhesive patch according to the present disclosure may be improved by the width of the micro channel groove and a height difference between each relief and the hydrogel layer. Further, even when the hydrogel layer absorbs the moisture and expands, an area in contact with the adhered face may not be reduced or the adhesive strength may not be reduced.

In one embodiment, the adhesive patch includes the hydrogel layer disposed on the at least the portion of the bottom face of the micro channel groove and contained in the groove such that a vertical adhesive strength of the adhesive patch adhered to the adhered face may be equal to or greater than 1.2 N/cm$^2$.

In one embodiment, the adhesive patch includes the hydrogel layer disposed on the at least the portion of the bottom face of the micro channel groove such that a peel strength energy of the adhesive patch from the adhered face may be equal to or higher than 3 J/m$^2$.

An adhesive patch for another purpose of the present disclosure is an adhesive patch including a hydrogel layer having a pattern formed of a hydrogel formed thereon. Further, a hydrophobic relief is included between the pattern portions of the hydrogel layer.

In one embodiment, the hydrogel layer having the pattern formed of the hydrogel is included on the patch, and each relief may be formed by filling a hydrophobic substance in a groove where the pattern is not formed.

In one embodiment, in the hydrogel layer, a height of the pattern may be smaller than a height of each relief.

An adhesive patch for delivering a substance for another purpose of the present disclosure is an adhesive patch for delivering a drug or cosmetics, including the adhesive patch according to the present disclosure. The patch includes a drug, a drug-containing particle, or a cosmetic substance.

In one embodiment, the drug, the drug-containing particle, or the cosmetic substance may be contained in the patch, and may also be delivered into a skin when the adhesive patch is brought into contact with the skin.

In one embodiment, the drug, the drug-containing particle, or the cosmetic substance may be contained in a surface of each relief of the patch.

An adhesive patch for measuring a bio-signal for another purpose of the present disclosure is an adhesive patch for measuring a bio-signal of a skin, and includes the adhesive patch of the present disclosure, so that the adhesive patch for measuring the bio-signal may be adhered to a wet adhered face. Further, the adhesive patch for measuring the bio-signal includes a piezoelectric layer adhered to a face of the patch opposite to the surface portion or inserted into the patch such that the piezo electric layer is deformed along with a mechanical deformation of the adhesive patch, and includes an electrode for receiving an electrical signal from the piezoelectric layer.

In one embodiment, each relief may include a conductive polymer to receive an electrical signal.

FIG. 1 illustrates a schematic diagram of an adhesive patch according to an embodiment of the present disclosure, which is shown to describe a patch with a high adhesive strength based on biomimetics. The patch is a dry-type adhesion system developed by researching and simulating an adhesive system of a mollusc in nature. In FIG. 1, the patch has nano/micro structures of various forms formed on a surface thereof. Specifically, the adhesive patch according to one embodiment of the present disclosure may include a plurality of micro channels (reliefs), a hydrogel pattern hydrogel layer formed with a hydrogel disposed in a micro channel groove in the micro channel structure, and a micro pattern structure defined in a portion of a surface of the micro channel structure. The hydrogel may be inserted into the micro channel groove defined between the plurality of reliefs to form the hydrogel layer. Alternatively, the adhesive patch may include the hydrogel pattern formed of the hydrogel formed thereon, and the reliefs may be included between hydrogel pattern portions, or a portion on the patch where the hydrogel pattern is not formed. In this connection, the patch may be produced using biocompatible polymers to be applicable to a living body. Therefore, even when the patch is adhered to a surface of the living body for a long time, less irritation occurs on an adhered face. Because of the micro channel structure, not entirety of a face of the patch is adhered to the adhered face, so that the patch has a permeability. Further, since the hydrogel is inserted into the micro channel groove, moisture may be absorbed and discharged, so that control of the moisture may be achieved. Therefore, an adhesive strength of the patch may not be reduced even on a wet surface.

Figure 2:
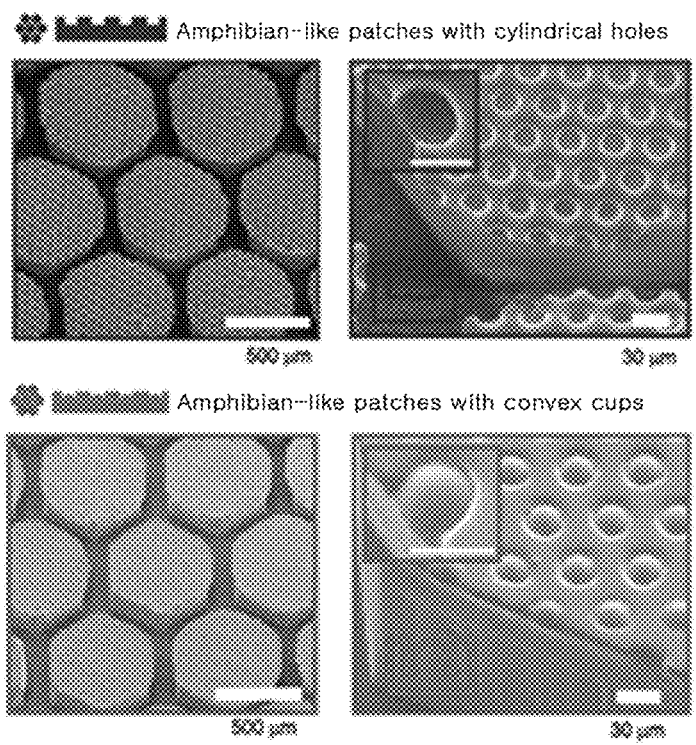
FIG. 2 illustrates a portion of a patch according to an embodiment.

FIG. 2 illustrates a portion of a patch according to an embodiment of the present disclosure. FIG. 2 shows images, which are results of analyzing the micro pattern structures defined in the patch. FIG. 2 shows that the micro pattern structure of the patch is a cup-shaped hole pattern with a flat bottom face, or a hole pattern with a convex bottom face. Although not shown in FIG. 2, the micro pattern structure may be formed in various forms, and may include a needle or protrusion of a nano size or micro size. Further, such micro pattern structure may contain a drug, cosmetics, or the like therein.

Figure 3A:
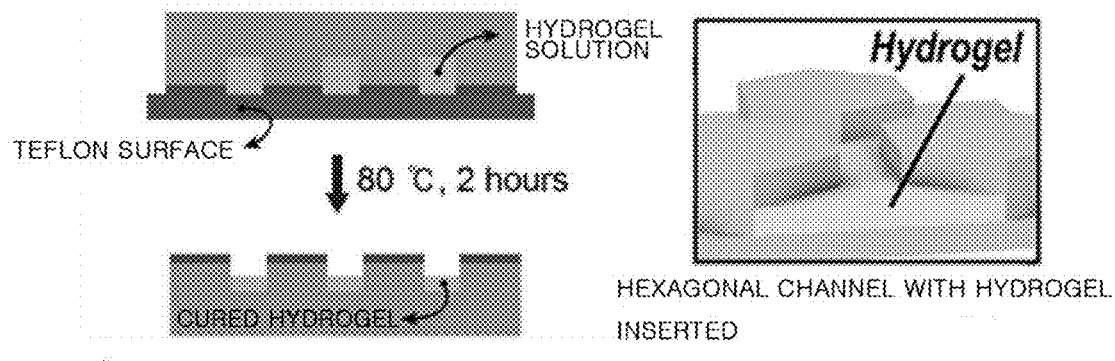
FIGS. 3A and 3B illustrate a patch according to an embodiment.
Figure 3B:
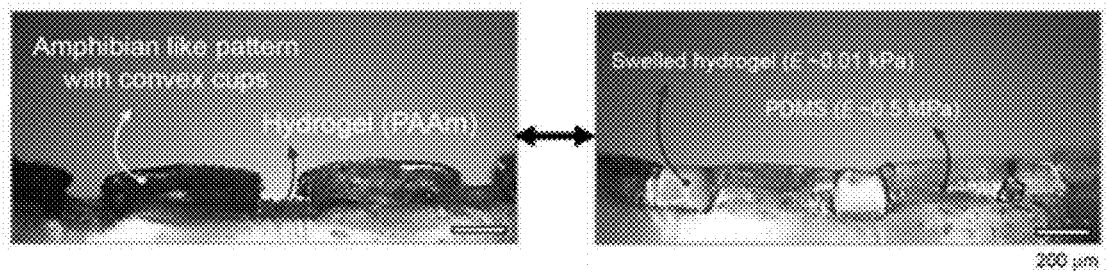

FIGS. 3A-3B illustrate a patch according to an embodiment. FIG. 3A is a schematic diagram illustrating a portion of a method for producing the adhesive patch. Further, FIG. 3B illustrates a result of microscopic observation of a portion of an actual patch produced based on the method for producing the adhesive patch. In FIG. 3A, an adhesive patch including a hydrogel layer was produced by contacting a face on which a micro channel structure is formed of a patch with a Teflon substrate, then inserting a hydrogel into a micro channel groove, then curing the inserted hydrogel for 2 hours at 80° C. An image in which the hydrogel is actually inserted into the micro channel groove may be seen in FIG. 3B.

Figure 4A:
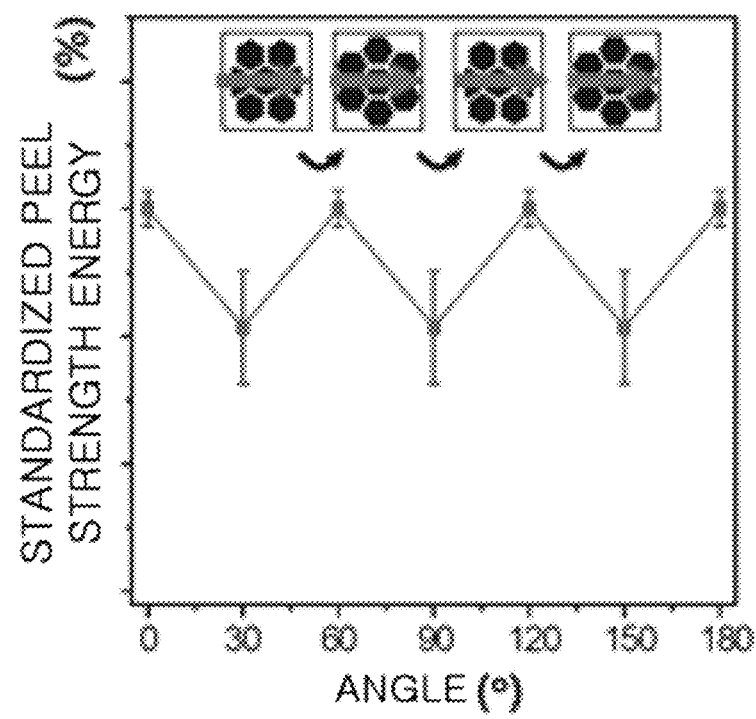
FIGS. 4A-4C illustrate an effect of a patch according to an embodiment.
Figure 4B:
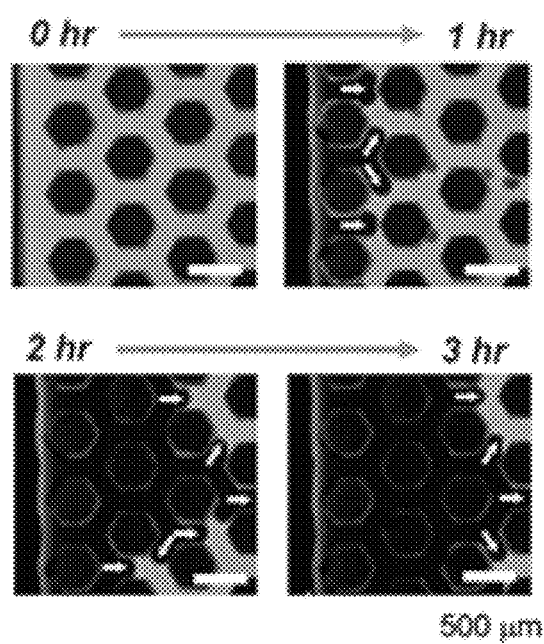
Figure 4C:
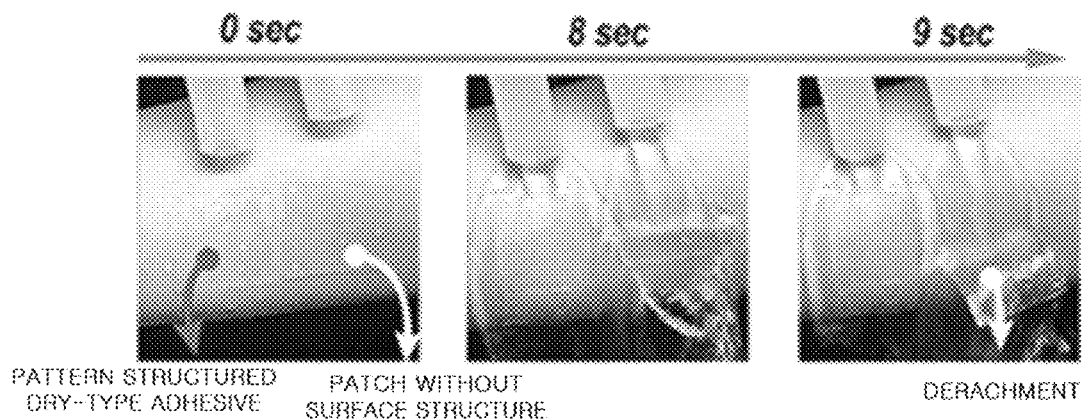

FIGS. 4A-4C illustrate an effect of a patch according to an embodiment. Specifically, FIG. 4A is a graph showing a result of an experiment of peel strengths in various directions of an adhesive patch according to an embodiment of the present disclosure. Further, FIGS. 4B and 4C show a fluorescence microscopic observation result and actual images showing effects of moisture absorption and emission control through the micro-channel structure of the patch. It may be seen that, since the micro channel structure is formed on the adhesive patch, peel strength energies based on directions are different due to the pattern of the structure. Further, in FIG. 4B, it may be seen that the hydrogel layer of the adhesive patch absorbs and discharges the moisture over time. Further, in FIG. 4C, adhesive strengths based on whether the micro pattern structure exists were compared with each other. It may be seen that a patch in which the micro pattern structure is not formed is detached within 10 seconds when water flows on the adhered face, and a patch in which the micro pattern structure is formed is adhered well to the adhered face even when the water flows on the adhered face.

Figure 5:
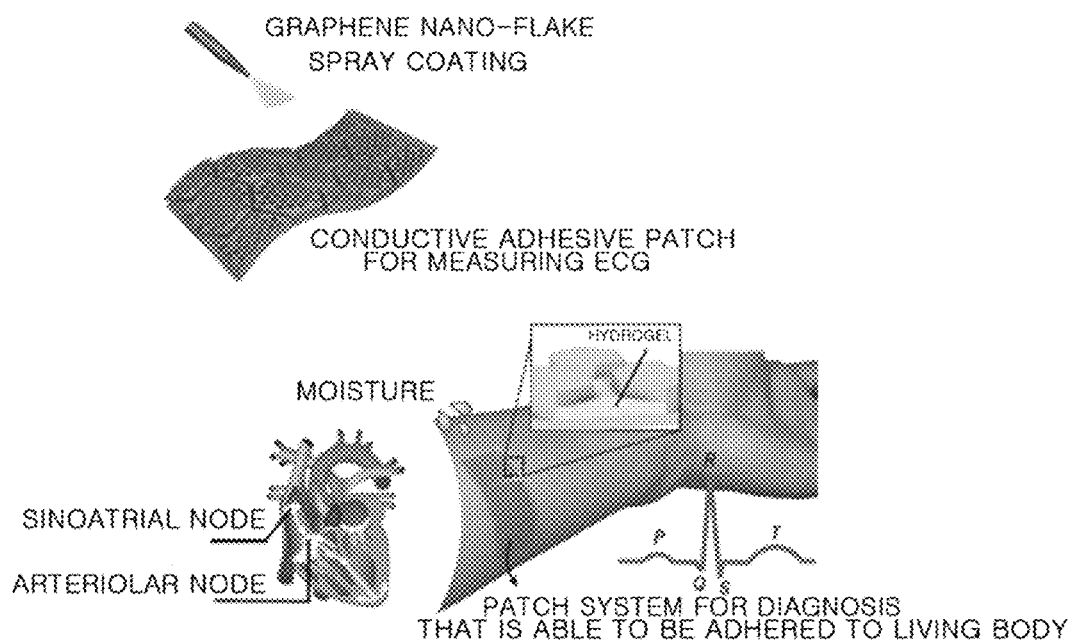
FIG. 5 illustrates an adhesive patch for measuring a bio-signal according to an embodiment of the present disclosure.

FIG. 5 illustrates an adhesive patch for measuring a bio-signal according to an embodiment of the present disclosure. FIG. 5 simply shows a method for coating graphene nano-flakes on an adhesion face of the adhesive patch according to the present disclosure. A conductive adhesive patch for a living body may be produced using such technology. The patch thus produced is based on a physical adhesion principle such as a van der Waals force, an adsorption effect, a capillary phenomenon, and the like, and the hydrogel layer that may control the moisture absorption and discharge is included. Thus, a medical wearable element for measuring a bio-signal that minimizes irritation on the adhered face and has excellent adhesive strength and sensitivity in the moisture environment may be produced without the separate chemical adhesive using the patch thus produced.

Figure 6A:
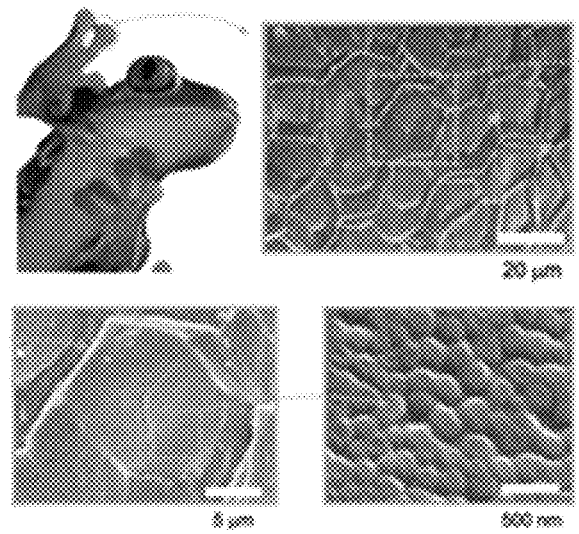
FIGS. 6A-6B illustrate a patch and a method for producing the same according to an embodiment.
Figure 6B:
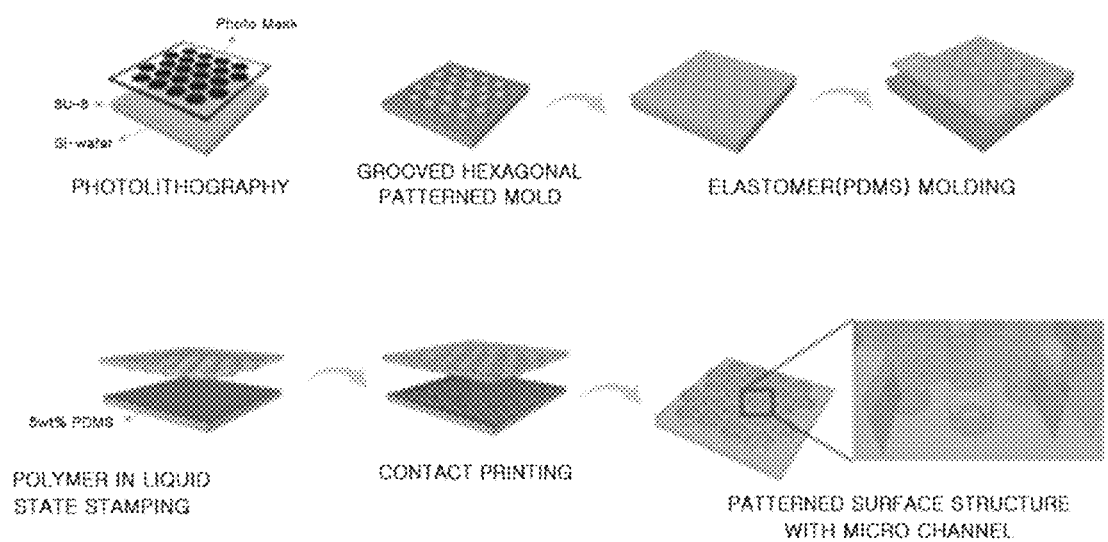

FIGS. 6A-6B illustrate an example of an adhesive patch and a method for producing the same. In FIG. 6A, it may be seen that there are hexagonal micro channel structures and microstructures on a toe surface of an amphibian. Such structures may be formed using low cost production processes of photolithography, solution process-based elastomeric patterning, and contact printing. In FIG. 6B, the photolithography thereamong was used. First, a mold of a hexagonal groove shape was produced using the photolithography, and a micro hexagonal pattern based on an elastomer was produced using the mold and a polymer precursor. Then, polymer in a liquid state was stamped on the surface of the patch on which the hexagonal pattern was formed, which was contact-printed on a micro pattern structure mold of another size to produce the micro pattern structure.

Then, the surface of the patch having the produced micro channel and micro pattern structure was subjected to a plasma treatment and was placed on a glass or a Teflon substrate. When a hydrogel precursor flows through the channel groove toward a side of the patch, the hydrogel is easily inserted by a microfluidic phenomenon. Thereafter, the hydrogel was cured to produce the adhesive patch according to the present disclosure.

Figure 7A:
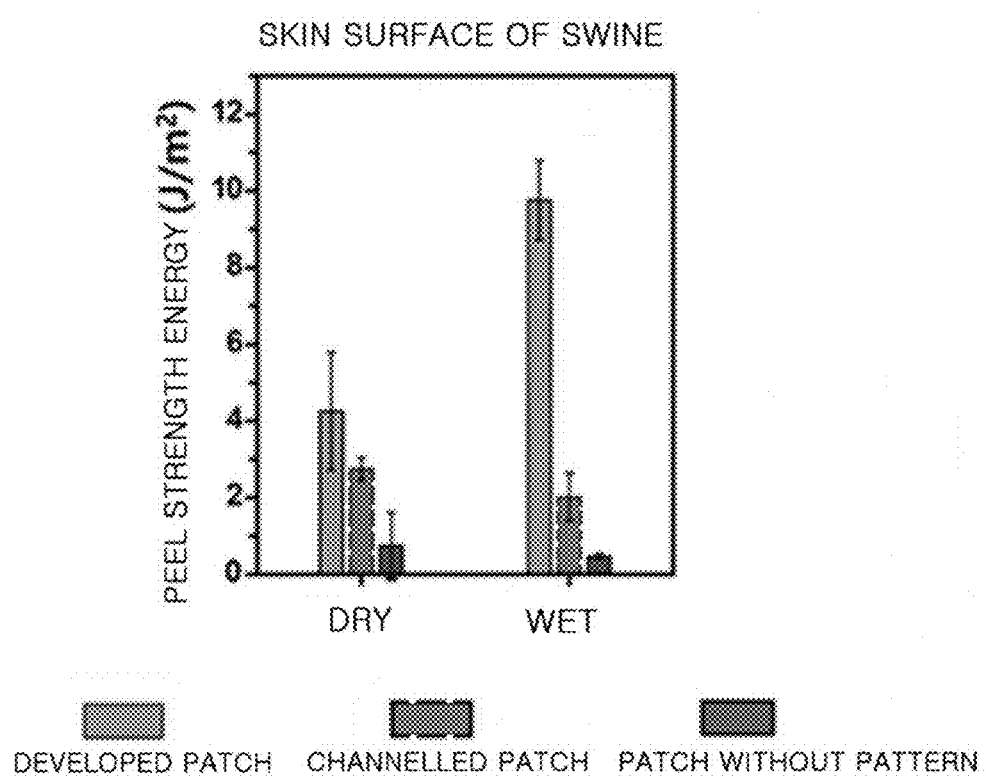
FIGS. 7A-7B illustrate an effect of a patch according to an embodiment.
Figure 7B:
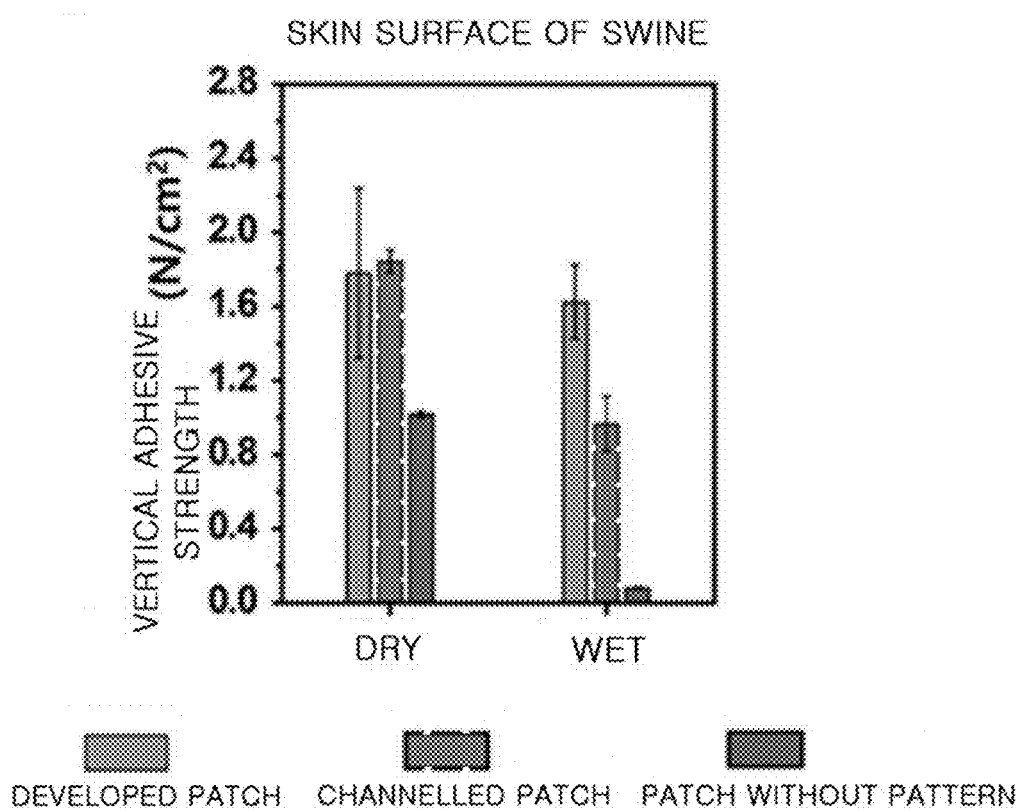

FIGS. 7A-7B illustrate an effect of a patch according to an embodiment. FIG. 7A is a graph comparing peel strength energies of the adhesive patch according to an embodiment of the present disclosure with each other. Further, FIG. 7B is a graph showing vertical adhesive strengths. In FIG. 7A, the patch on which the microchannel structure is not formed shows a very low peel strength energy whether a skin surface of a swine is dry or wet, and a vertical adhesive strength thereof is also very low. Further, the patch on which the micro channel structure is formed and the adhesive patch containing the hydrogel in the micro channel structure according to the present disclosure have peel strength energies and vertical adhesive strengths higher than that of the patch on which the micro channel structure is not formed, in both dry and wet conditions. In particular, the adhesive patch containing the hydrogel in the micro channel structure according to the present disclosure shows significantly high peel strength energy and vertical adhesive strength even when the skin surface of the swine is wet.

Hereinabove, although the present disclosure has been described with reference to the preferred embodiments of the present disclosure, the present disclosure is not limited thereto, but may be variously modified and altered by those skilled in the art to which the present disclosure pertains without departing from the spirit and scope of the present disclosure claimed in the following claims.

What is claimed is:

1. An adhesive patch having a surface portion, the surface portion comprising:
    a plurality of reliefs, each relief having a flat top face; and
    a hydrogel layer configured to absorb water and disposed in a micro channel groove defined between adjacent reliefs of the plurality of reliefs,
    wherein the plurality of reliefs and the micro channel groove are respectively formed on and defined in a surface of the adhesive patch, and
    wherein the hydrogel layer is disposed on at least a portion of a bottom face of the micro channel groove and is contained in the micro channel groove.

2. The adhesive patch of claim 1, wherein a height of the hydrogel layer from the bottom face of the micro channel groove is smaller than a height of each relief from the bottom face of the micro channel groove.

3. The adhesive patch of claim 1, wherein a contact angle of a water droplet on the hydrogel layer is smaller than a contact angle of a water droplet on each relief.

4. The adhesive patch of claim 1, wherein a contact angle of a water droplet on the hydrogel layer is equal to or smaller than 70°.

5. The adhesive patch of claim 1, wherein the hydrogel layer absorbs and discharges moisture.

6. The adhesive patch of claim 1, wherein the hydrogel layer includes at least one selected from a group consisting of poly acrylamide (PAAm), poly(N-isopropylacrylamide) (PNIPAM), poly ethylene glycol (PEG), chitosan, polyallylamine (PAA), polyethylenimine (PEI), collagen, gelatin, polyampholyte (PA), poly(2-hydroxyethyl methacrylate)-co-poly-(ethylene glycol) diacrylate (PHEMA-co-PEGDA), poly(dimethyl diallyl ammonium chloride)/tannic acid, alginate, and mixtures thereof.

7. The adhesive patch of claim 3, wherein the hydrogel layer has a hydrophile-lipophile balance (HLB) value of 5 to 20.

8. The adhesive patch of claim 3, wherein each relief has a hydrophile-lipophile balance (HLB) value of 0 to 15.

9. The adhesive patch of claim 1, wherein each relief includes at least one selected from a group consisting of natural rubber, nitrile rubber, acrylonitrile-butadiene rubber, styrenebutadiene rubber, chloroprene rubber, butyl rubber, isoprene-isobutylene rubber, ethylene propylene rubber, chlorosulphonated polyethylene rubber, acrylic rubber, fluoro rubber, polysulfide rubber, silicone rubber, butadiene rubber, isoprene rubber, urethanerubber, polyurethane, polyolefin thermoplastic elastomer (TPE), polystyrene TPE, polyvinyl chloride TPE, polyester TPE, polyurethane TPE, polyamide TPE, polyethyleneterephthalate (PET), polydimethylsiloxane (PDMS), polyurethaneacrylate, polyethylenenaphthalate (PEN), and mixtures thereof.

10. An adhesive patch having a surface portion, the surface portion comprising:
a plurality of reliefs, each relief having a flat top face; and
a micro channel groove defined between adjacent reliefs of the plurality of reliefs,
wherein the plurality of reliefs and the micro channel groove are respectively formed on and defined in a surface of the adhesive patch,
wherein a hydrogel layer is disposed on at least a portion of a bottom face of the micro channel groove and is contained in the micro channel groove,
wherein the adhesive patch is configured to be adhered to an adhered face, and
wherein the adhered face contains moisture or oil.

11. The adhesive patch of claim 1, wherein the adhesive patch is configured to be adhered to an adhered face, and
wherein the adhered face contains 25 µl or smaller of water per 1 cm² of the adhered face.

12. The adhesive patch of claim 1, wherein the adhesive patch is configured to be adhered to an adhered face, and
wherein the adhered face is a skin.

13. The adhesive patch of claim 1, wherein the adhesive patch is configured to be adhered to an adhered face, and
wherein a width of each micro channel groove is sized such that moisture is sucked into a space between the adhered face and the hydrogel layer in the micro channel groove via a capillary force.

14. The adhesive patch of claim 13, wherein the width of the micro channel groove is in a range of 1 nm to 1000 µm.

15. The adhesive patch of claim 14, wherein the hydrogel layer is disposed on at least a portion of the bottom face of the micro channel groove and is contained in the groove such that a vertical adhesive strength of the adhesive patch adhered to the adhered face is equal to or greater than 1.2 N/cm².

16. The adhesive patch of claim 14, wherein the hydrogel layer is disposed on at least a portion of the bottom face of the micro channel groove such that a peel strength energy of the adhesive patch from the adhered face is equal to or greater than 3 J/m².

17. An adhesive patch for delivering a substance, the adhesive patch having a surface portion comprising:
a plurality of reliefs, each relief having a flat top face; and
a micro channel groove defined between adjacent reliefs of the plurality of reliefs,
wherein the plurality of reliefs and the micro channel groove are respectively formed on and defined in a surface of the adhesive patch,
wherein a hydrogel layer is disposed on at least a portion of a bottom face of the micro channel groove and is contained in the micro channel groove, and
wherein the adhesive patch contains a drug, a drug-containing particle, or a cosmetic substance.

18. The adhesive patch of claim 17, wherein the drug, the drug-containing particle, or the cosmetic substance contained in the adhesive patch is delivered into the skin when the adhesive patch is brought into contact with the skin.

19. The adhesive patch of claim 17, wherein the drug, the drug-containing particle, or the cosmetic substance is contained in a surface of each relief.

20. An adhesive patch for measuring a bio-signal of a skin, the adhesive patch including the adhesive patch of claim 1,
wherein the adhesive patch is configured to be adhered to a wet adhered face,
wherein the adhesive patch further includes:
a piezoelectric layer adhered to a face of the patch opposite to the surface portion or inserted into the patch such that the piezo electric layer is deformed along with a mechanical deformation of the adhesive patch; and
an electrode for receiving an electrical signal from the piezoelectric layer.

21. The adhesive patch of claim 1, wherein each relief having the flat top face comprises micro pattern structures defined therein.

* * * * *